United States Patent
Zhang et al.

(10) Patent No.: US 11,815,511 B2
(45) Date of Patent: *Nov. 14, 2023

(54) TIME-RESOLVED FLUORESCENCE KIT FOR SYNCHRONOUSLY DETECTING 4,15-DIACETOXYSCIRPENOL, DEOXYNIVALENOL, AND T-2 TOXIN

(71) Applicant: OIL CROPS RESEARCH INSTITUTE, CHINESE ACADEMY OF AGRICULTURAL SCIENCES, Hubei (CN)

(72) Inventors: Qi Zhang, Hubei (CN); Xiaoqian Tang, Hubei (CN); Yizhen Bai, Hubei (CN); Wen Zhang, Hubei (CN); Peiwu Li, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/777,268

(22) PCT Filed: Nov. 16, 2020

(86) PCT No.: PCT/CN2020/129074
§ 371 (c)(1),
(2) Date: May 16, 2022

(87) PCT Pub. No.: WO2021/093886
PCT Pub. Date: May 20, 2021

(65) Prior Publication Data
US 2022/0412965 A1    Dec. 29, 2022

(30) Foreign Application Priority Data
Nov. 15, 2019  (CN) .......................... 201911122507.3

(51) Int. Cl.
*G01N 33/533* (2006.01)
*G01N 33/558* (2006.01)
*G01N 33/577* (2006.01)

(52) U.S. Cl.
CPC .......... *G01N 33/533* (2013.01); *G01N 33/558* (2013.01); *G01N 33/577* (2013.01)

(58) Field of Classification Search
CPC .. G01N 33/533; G01N 33/558; G01N 33/577; G01N 33/54387; G01N 33/54388;
(Continued)

(56) References Cited

U.S. PATENT DOCUMENTS 6,187,203 B1    2/2001    Tseng

FOREIGN PATENT DOCUMENTS

| CN | 102798714 | 11/2012 |
|---|---|---|
| CN | 104535664 | 4/2015 |

(Continued)

OTHER PUBLICATIONS

Xiaoqian Tang et al., "Rapid, on-site and quantitative paper-based immunoassay platform for concurrent determination of pesticide residues and mycotoxins", Analytica Chimica Acta, Jun. 2019, pp. 142-150.
(Continued)

*Primary Examiner* — Christopher L Chin
(74) *Attorney, Agent, or Firm* — JCIP GLOBAL INC.

(57) ABSTRACT

A time-resolved fluorescence kit for synchronously detecting 4,15-diacetoxyscirpenol, deoxynivalenol and T-2 toxin. The kit includes an immunochromatography time-resolved fluorescence test strip and a sample reaction bottle containing freeze-dried products of europium-labeled monoclonal antibodies of toxins, where the immunochromatography time-resolved fluorescence test strip includes a liner, where a water absorption pad, a detection pad and a sample pad are
(Continued)

sequentially attached to one side of the liner from top to bottom, adjacent pads are connected in an overlapping manner at a joint, the detection pad uses a nitrocellulose membrane as a base pad, a transverse quality control line and detection lines are arranged on the nitrocellulose membrane from top to bottom, the quality control line is coated with a rabbit antimouse polyclonal antibody, the three detection lines are located below the quality control line, and the detection lines each are coated with a toxin-protein conjugate.

10 Claims, 2 Drawing Sheets

Specification includes a Sequence Listing.

(58) Field of Classification Search
CPC .......... G01N 33/54389; G01N 33/582; G01N 2800/709; B01L 2300/0825
USPC ....... 422/400, 401, 420, 421, 425, 426, 430; 435/287.7, 287.9, 970, 805, 810; 436/169, 170, 514, 518, 530, 810
See application file for complete search history.

(56) References Cited

FOREIGN PATENT DOCUMENTS

| | | |
|---|---|---|
| CN | 104693304 | 6/2015 |
| CN | 107727781 | 2/2018 |
| CN | 107942062 | 4/2018 |
| CN | 109894166 | 6/2019 |
| CN | 111007246 | 4/2020 |
| CN | 111007247 | 4/2020 |
| EP | 3502698 | 6/2019 |

OTHER PUBLICATIONS

Richard Dietrich et al., "Use of Monoclonal Antibodies for the Analysis of Mycotoxins", Natural Toxins, Jan. 1995, pp. 288-293.
"Office Action of China Counterpart Application", dated Mar. 1, 2021, with English translation thereof, pp. 1-18.
"Notification of Grant of China Counterpart Application", dated Aug. 24 1, 2021, with English translation thereof, pp. 1-3.
"International Search Report (Form PCT/ISA/210) of PCT/CN2020/ 129074" dated Jan. 29, 2021, with English translation thereof, pp. 1-7.

SEQUENCE LISTING

```
<160> NUMBER OF SEQ ID NOS: 4

<210> SEQ ID NO 1
<211> LENGTH: 351
<212> TYPE: DNA
<213> ORGANISM: Mice

<400> SEQUENCE: 1
gaagtgcaac tggtggagtc tgggggagac ttagtgaagc ctggagggtc cctgaaactc     60
tcctgttcag cctccggatt cactttcaat tactatggca tgtcttgggt tcgccagact    120
ccagacaacc tcctggagtg ggtcgcaggc attagtagtg gtggttctta cacctattat    180
tctgacagtg tgaagggacg attcaccatc tccagagaca gtgccacgaa caccctgtac    240
ctgcaaatga ccagtctgaa gtctcaagac acagccatgt attattgtat tagactcccg    300
tttgggtcta tggactattg gggtcaagga accgcagtca ccgtctcctc a             351

<210> SEQ ID NO 2
<211> LENGTH: 324
<212> TYPE: DNA
<213> ORGANISM: Mice

<400> SEQUENCE: 2
caggctgttg tgactcagga acctgcactc accacatcac ctggtgaaac agtcacactc     60
acttgtcgct caagtactgg ggctgtaaca actggtaatt atgtcaactg ggtccaagag    120
aaaccagatc atttattcag tggtctaata ggtaatacca ataaccgagc tccaggtgtt    180
cctgccagat tctcaggctc cctgattgga gacaaggctg ccctcaccat cacagggaca    240
cagactgagg atgaggcaat atatttctgt gctctatggt acaccgacca tttggtgttc    300
ggtggaggaa ccaaattgac tgtc                                           324

<210> SEQ ID NO 3
<211> LENGTH: 117
<212> TYPE: PRT
<213> ORGANISM: Mice
```

-continued

```
<400> SEQUENCE: 3

Glu Val Gln Leu Val Glu Ser Gly Gly Asp Leu Val Lys Pro Gly Gly
1               5                   10                  15

Ser Leu Lys Leu Ser Cys Ser Ala Ser Gly Phe Thr Phe Asn Tyr Tyr
            20                  25                  30

Gly Met Ser Trp Val Arg Gln Thr Pro Asp Asn Leu Leu Glu Trp Val
        35                  40                  45

Ala Gly Ile Ser Ser Gly Gly Ser Tyr Thr Tyr Tyr Ser Asp Ser Val
    50                  55                  60

Lys Gly Arg Phe Thr Ile Ser Arg Asp Ser Ala Thr Asn Thr Leu Tyr
65                  70                  75                  80

Leu Gln Met Thr Ser Leu Lys Ser Gln Asp Thr Ala Met Tyr Tyr Cys
                85                  90                  95

Ile Arg Leu Pro Phe Gly Ser Met Asp Tyr Trp Gly Gln Gly Thr Ala
            100                 105                 110

Val Thr Val Ser Ser
        115

<210> SEQ ID NO 4
<211> LENGTH: 108
<212> TYPE: PRT
<213> ORGANISM: Mice

<400> SEQUENCE: 4

Gln Ala Val Val Thr Gln Glu Pro Ala Thr Thr Thr Ser Pro Gly Glu
1               5                   10                  15

Thr Val Thr Leu Thr Cys Arg Ser Ser Thr Gly Ala Val Thr Thr Gly
            20                  25                  30

Asn Tyr Val Asn Trp Val Gln Glu Lys Pro Asp His Leu Phe Ser Gly
        35                  40                  45

Leu Ile Gly Asn Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Thr
65                  70                  75                  80

Gln Thr Glu Asp Glu Ala Ile Tyr Phe Cys Ala Leu Trp Tyr Thr Asp
                85                  90                  95

His Leu Val Phe Gly Gly Gly Thr Lys Leu Thr Val
            100                 105
```

TIME-RESOLVED FLUORESCENCE KIT FOR SYNCHRONOUSLY DETECTING 4,15-DIACETOXYSCIRPENOL, DEOXYNIVALENOL, AND T-2 TOXIN

This is a 371 application of the International PCT application serial no. PCT/CN2020/129074, filed on Nov. 16, 2020, which claims the priority benefits of China Application No. 201911122507.3, filed on Nov. 15, 2019. The entirety of each of the above-mentioned patent applications is hereby incorporated by reference herein and made a part of this specification.

BACKGROUND

Technical Field

The present disclosure relates to an immunochromatography time-resolved fluorescence test strip for mycotoxins and pesticides, in particular to a time-resolved fluorescence kit for synchronously detecting composite pollution of 4,15-diacetoxyscirpenol, deoxynivalenol, and T-2 toxin, and a preparation method.

Description of Related Art 4,15-diacetoxyscirpenol belongs to trichothecene mycotoxins, and is mainly produced by *Fusarium scirpi* and *Fusarium equiseti*. 4,15-diacetoxyscirpenol mainly pollutes grains and feed. Its detection rate in the feed is not higher than that of vomitoxin, its toxicity to animals is, however, higher than that of vomitoxin. Similar to T-2 toxin, 4,15-diacetoxyscirpenol may damage animal hematopoietic organs such as bone marrow, continuously reduce leucocytes, cause cardiomyopathy hemorrhage, and the like. Deoxynivalenol (DON) is also referred to as vomitoxin, can be accumulated in vivo, and has very strong cytotoxicity, immunotoxicity, embryotoxicity, and teratogenic effects, causing acute poisoning symptoms such as anorexia, vomiting, diarrhea, fever, unsteadiness and unresponsiveness of humans and animals and damaging a hematopoietic system to cause death in severe cases. UN Food and Agriculture Organization and World Health Organization have already determined deoxynivalenol as one of the most dangerous and naturally occurring food pollutants, and deoxynivalenol is listed in priorities of international research. T-2 toxin has the strongest toxicity in trichothecene mycotoxins. The foregoing three toxins all mainly pollute grain crops such as wheat, barley and corn, and products thereof, causing great harm to human health and animal husbandry. Since 4,15-diacetoxyscirpenol, deoxynivalenol, and T-2 toxin always cause composite pollution to grains, a convenient and rapid detection technology is needed to rapidly and synchronously screen these three types of pollutants, so as to meet a regulation requirement for controlling toxin pollution in agricultural products.

Currently, detecting methods for these toxins mainly include liquid chromatography, gas chromatography-mass spectrometry, liquid chromatography-mass spectrometry, and the like. These methods are high in stability, sensitivity, and accuracy, but preprocessing steps are complex and sample detection costs are high. Immunochromatography overcomes the foregoing defects. Based on antigen and antibody specific reactions, nitrocellulose is used to fix antigens, free targets in a chromatography process compete with the antigens on detection lines to bind to labeled antibodies, and a quantity of the targets contained in a sample is calculated by using a quantity of labels bound to the detection lines. Time-resolved fluorescence immunochromatographic assay (TRFICA) uses europium as a high-affinity probe, has the advantages of being high in sensitivity, stable in property, free from interference of fluorescence background, short in detection time, and the like, and is quite suitable for developing a pesticide residue rapid detection method.

Therefore, developing a time-resolved fluorescence kit for synchronously detecting composite pollution of 4,15-diacetoxyscirpenol (anguidin), deoxynivalenol, and T-2 toxin is of a great necessity and has quite important significance.

SUMMARY

To solve the problem, the present disclosure provides a time-resolved fluorescence kit capable of synchronously detecting composite pollution of 4,15-diacetoxyscirpenol, deoxynivalenol, and T-2 toxin, and a preparation method. The time-resolved fluorescence kit can be used to synchronously detect quantities of 4,15-diacetoxyscirpenol, deoxynivalenol, and T-2 toxin contained in a sample, and has the characteristics of simple and rapid operation and high sensitivity.

To solve the foregoing technical problem, the technical solution adopted by the present disclosure is as follows:

a time-resolved fluorescence kit for synchronously detecting 4,15-diacetoxyscirpenol, deoxynivalenol, and T-2 toxin includes an immunochromatography time-resolved fluorescence test strip and a sample reaction bottle containing freeze-dried products of an europium-labeled anti-4,15-diacetoxyscirpenol monoclonal antibody, an europium-labeled anti-deoxynivalenol monoclonal antibody, and an europium-labeled anti-T-2 toxin monoclonal antibody, where the immunochromatography time-resolved fluorescence test strip includes a liner, where a water absorption pad, a detection pad, and a sample pad are sequentially attached to one side of the liner from top to bottom, adjacent pads are connected in an overlapping manner at a joint, the detection pad uses a nitrocellulose membrane as a base pad, a transverse quality control line and detection lines are arranged on the nitrocellulose membrane from top to bottom, the quality control line is coated with a rabbit anti-mouse polyclonal antibody, the three detection lines are located below the quality control line, and the detection lines are coated with a 4,15-diacetoxyscirpenol-bovine serum albumin conjugate, a deoxynivalenol-bovine serum albumin conjugate, and a T-2 toxin-ovalbumin conjugate respectively; and the anti-4,15-diacetoxyscirpenol monoclonal antibody is secreted by a hybridoma cell strain DAS5G11E7 with the preservation number of CCTCC NO:C201881 and this hybridoma cell strain DAS5G11E7 has already been preserved on Apr. 3, 2018 in China Center For Type Culture Collection (CCTCC), the preservation address is Wuhan University, Wuhan, China, and the preservation number is CCTCC NO. C201881.

According to the foregoing solution, the europium-labeled anti-4,15-diacetoxyscirpenol monoclonal antibody is prepared by using the following method: evenly mixing an europium labeling reagent and a 4,15-diacetoxyscirpenol monoclonal antibody according to a mass ratio of 1:(0.04-0.3), oscillating on a shaking table for 2 h to 4 h, centrifuging to remove supernate, and blocking redundant binding sites on a surface of the europium labeling reagent to obtain the target product, namely the europium-labeled anti-4,15-diacetoxyscirpenol monoclonal antibody;

the europium-labeled anti-deoxynivalenol monoclonal antibody is prepared by using the following method: evenly mixing an europium labeling reagent and a deoxynivalenol monoclonal antibody according to a mass ratio of 1:(0.04-0.3), oscillating on a shaking table for 2 h to 4 h, centrifuging to remove supernate, and blocking redundant binding sites on a surface of the europium labeling reagent to obtain the target product, namely the europium-labeled anti-deoxynivalenol monoclonal antibody; and the europium-labeled anti-T-2 toxin monoclonal antibody is prepared by using the following method: evenly mixing an europium labeling reagent and a T-2 toxin monoclonal antibody according to a mass ratio of 1:(0.04-0.3), oscillating on a shaking table for 2 h to 4 h, centrifuging to remove supernate, and blocking redundant binding sites on a surface of the europium labeling reagent to obtain the target product, namely the europium-labeled anti-T-2 toxin monoclonal antibody.

According to the foregoing solution, the europium labeling reagent is activated before use, and the activation includes: dissolving the europium labeling reagent in a boric acid buffer solution, oscillating and evenly mixing, adding an EDC solution, oscillating and activating for 15 min to 30 min, centrifuging at 10000 rpm to 15000 rpm, adding a boric acid buffer solution, oscillating and evenly mixing, and ultrasonically processing.

According to the foregoing solution, a blocking solution for blocking is a boric acid buffer solution that contains 0.5% to 1% of BSA.

According to the foregoing solution, in the immunochromatography time-resolved fluorescence test strip, the water absorption pad is 15 mm to 35 mm in length and 3 mm to 5 mm in width, the sample pad is 12 mm to 18 mm in length and 2 mm to 5 mm in width, and an overlapping length of adjacent pads is 1 mm to 3 mm; on the detection pad in the immunochromatography time-resolved fluorescence test strip, a distance between the detection line close to the quality control line and an upper edge of the nitrocellulose membrane is 15 mm to 20 mm, a distance between every two adjacent detection lines is 1.5 mm to 4.5 mm, and a distance between the detection line close to the quality control line and the quality control line and detection lines is 4 mm to 10 mm; and the sample reaction bottle is a 1-5 mL bayonet bottle.

According to the foregoing solution, on the detection pad in the immunochromatography time-resolved fluorescence test strip, a coating quantity of the 4,15-diacetoxyscirpenol-bovine serum albumin conjugate required for each centimeter of detection line is 0.4 µg to 0.8 µg, a coating quantity of the deoxynivalenol-bovine serum albumin conjugate required for each centimeter of detection line is 0.8 µg to 1.0 µg, and a coating quantity of the T-2 toxin-ovalbumin conjugate required for each centimeter of detection line is 0.8 µg to 1.0 µg; and a quantity of the freeze-dried product of the europium-labeled anti-4,15-diacetoxyscirpenol monoclonal antibody contained in the sample reaction bottle is 0.1 µg to 0.3 µg, a quantity of the freeze-dried product of the europium-labeled anti-deoxynivalenol monoclonal antibody contained in the sample reaction bottle is 0.2 µg to 0.4 µg, and a quantity of the freeze-dried product of the europium-labeled anti-T-2 toxin monoclonal antibody contained in the sample reaction bottle is 0.2 µg to 0.4 µg.

According to the foregoing solution, preferably, an IC50 of the anti-deoxynivalenol monoclonal antibody is less than or equal to 15 ppb.

According to the foregoing solution, an IC50 of the anti-T-2 toxin monoclonal antibody is less than or equal to 2 ppb.

According to the foregoing solution, the time-resolved fluorescence kit for synchronously detecting composite pollution of 4,15-diacetoxyscirpenol, deoxynivalenol, and T-2 toxin further includes a sample diluent, where the sample diluent includes 0.01% to 0.30% by volume of Tween®-20, 0.5% to 1.5% by volume of sucrose, and 0.1% to 1% by volume of a bovine serum albumin (BSA) aqueous solution by volume percentage.

According to the foregoing solution, a preparation method for the time-resolved fluorescence test strip includes the following steps:

(1) cutting water absorption paper into the water absorption pad;

(2) preparation of the detection pad:

preparing coating solutions with a concentration of 0.25 mg/mL to 2 mg/mL from the 4,15-diacetoxyscirpenol-bovine serum albumin conjugate, the deoxynivalenol-bovine serum albumin conjugate, and the T-2 toxin-ovalbumin conjugate, coating the nitrocellulose membrane with the coating solutions at intervals in a streak manner to obtain the three detection lines, respectively, and drying at 37° C. to 40° C. for 30 min to 60 min; where a coating quantity of the 4,15-diacetoxyscirpenol-bovine serum albumin conjugate required for each centimeter of the detection line coated with the 4,15-diacetoxyscirpenol-bovine serum albumin conjugate is 0.2 µg to 0.8 µg, a coating quantity of the deoxynivalenol-bovine serum albumin conjugate required for the detection line coated with the deoxynivalenol-bovine serum albumin conjugate is 0.2 µg to 1.0 µg, and a coating quantity of the T-2 toxin-ovalbumin conjugate required for the detection line coated with the T-2 toxin-ovalbumin conjugate is 0.2 µg to 1.0 µg;

on the detection pad in the immunochromatography time-resolved fluorescence test strip, a distance between the detection line close to the quality control line and an upper edge of the nitrocellulose membrane is 15 mm to 20 mm, a distance between every two adjacent detection lines is 1.0 mm to 5.5 mm, and a distance between the detection line close to the quality control line and the quality control line is 5 mm to 10 mm; and preparing a coating solution with a concentration of 0.1 mg/mL to 0.45 mg/mL from the rabbit antimouse polyclonal antibody, and transversely coating the nitrocellulose membrane with the coating solution in a position 5 mm to 10 mm away from the detection lines in a streak manner to obtain the quality control line, where a coating quantity of the rabbit antimouse polyclonal antibody required for each centimeter of the quality control line is 0.4 µg to 0.8 µg; and then, drying at 37° C. to 40° C. for 30 min to 60 min;

(3) preparation of the sample pad:

putting a fiberglass membrane into a blocking solution to be soaked, taking out the soaked fiberglass membrane, and drying at 37° C. to 40° C. for 4 h to 10 h to obtain the sample pad, and then preserving the sample pad in a dryer at room temperature; and (4) assembling of the immunochromatography time-resolved fluorescence test strip:

sequentially attaching the water absorption pad, the detection pad, and the sample pad to one side of a paperboard from top to bottom to obtain the immunochromatography time-resolved fluorescence test strip, where adjacent pads are connected in an overlapping manner at a joint, and an overlapping length is 1 mm to 3 mm.

According to the foregoing solution, during the preparation of the immunochromatography time-resolved fluorescence test strip, a coating buffer solution used to prepare the 4,15-diacetoxyscirpenol-bovine serum albumin conjugate coating solution, the deoxynivalenol-bovine serum albumin conjugate coating solution, and the T-2 toxin-ovalbumin conjugate coating solution includes in each 10 mL: 0.1 g of bovine serum albumin, 0.002 g of sodium azide, 0.08 g of sodium chloride, 0.029 g of sodium phosphate dibasic dodecahydrate, 0.002 g of potassium chloride, and 0.002 g of monopotassium phosphate;

a coating buffer

DESCRIPTION OF THE EMBODIMENTS

Obtaining of anti-4,15-diacetoxyscirpenol monoclonal antibody

An anti-4,15-diacetoxyscirpenol monoclonal antibody was secreted by a hybridoma cell strain DAS5G11E7 with the preservation number of CCTCC NO. C201881. A preparation method included:

injecting the hybridoma cell strain DAS5G11E7 into BALB/c mice preprocessed by using a Freund's incomplete adjuvant, collecting ascites of the mice, and purifying the antibody by using a caprylic acid-ammonium sulfate method. Specific operation included: filtering the ascites of the mice by using double-layer filter paper, centrifuging at 4° C. and 12000 r/min for 15 min or above, sucking supernate, mixing the ascites supernate with 4 times volume of an acetate buffer solution, slowly adding n-caprylic acid while stirring, with 30 µL to 35 µL of n-caprylic acid required for each mL of ascites, mixing at room temperature for 30 min to 60 min, and standing at 4° C. for 2 h or above; centrifuging at 12000 r/min and 4° C. for 30 min or above, discarding the obtained precipitate, filtering the resulting supernate by using double-layer filter paper, adding a phosphate buffer solution with a molar concentration of 0.1 mol/L and a pH of 7.4, with a volume being 1/10 that of the obtained filtrate, adjusting the pH of the mixed solution to 7.4 by using a 2 mol/L sodium hydroxide solution, slowly adding ammonium sulfate in an ice bath to reach an ammonium sulfate final concentration of 0.277 g/mL, standing at 4° C. for 2 h or above, then centrifuging at 12000 r/min and 4° C. for 30 min or above, discarding supernate, resuspending the resulting precipitate by using a phosphate buffer solution with a molar concentration of 0.01 mol/L and a pH of 7.4, with a volume being 1/10 that of the original ascites, filling a dialysis bag, dialyzing by using 0.01 mol/L PBS for 2 d, then dialyzing by using PB for 2 d, taking a protein solution out of the dialysis bag, centrifuging, collecting supernate, discarding the obtained precipitate, prefreezing at −70° C., and putting the prefrozen material into a freeze dryer for freeze-drying; and collecting freeze-dried powder, namely the purified anti-4,15-diacetoxyscirpenol monoclonal antibody.

The acetate buffer solution was prepared from 0.29 g of sodium acetate, 0.141 mL of acetic acid, and water that was added until a constant volume of 100 mL; the 0.01 mol/L phosphate buffer solution was prepared from 0.8 g of sodium chloride, 0.29 g of sodium phosphate dibasic dodecahydrate, 0.02 g of potassium chloride, and 0.02 g of monopotassium phosphate, and water that was added until a constant volume of 100 mL; and the 0.1 mol/L phosphate buffer solution was prepared from 8 g of sodium chloride, 2.9 g of sodium phosphate dibasic dodecahydrate, 0.2 g of potassium chloride, 0.2 g of monopotassium phosphate, and water that was added until a constant volume of 100 mL.

A subtype of the anti-4,15-diacetoxyscirpenol monoclonal antibody secreted by the hybridoma cell strain DAS5G11E7 was identified to be IgG2b by using a commercially available subtype identification kit.

Figure 3:
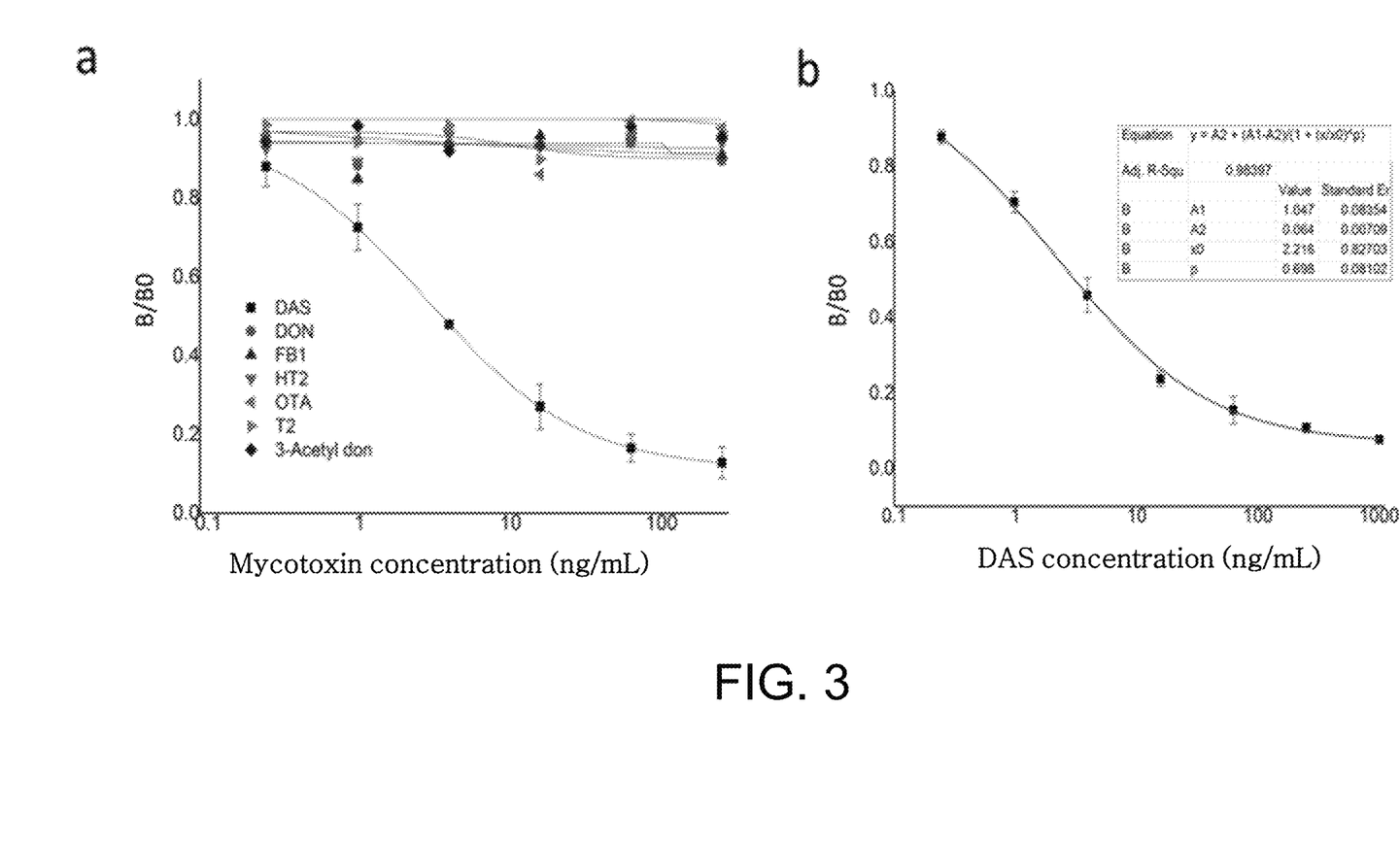
FIG. 3 illustrates a 4,15-diacetoxyscirpenol enzyme linked immunoassay standard curve constructed by a 4,15-diacetoxyscirpenol monoclonal antibody provided by the present disclosure.

It was measured by using a conventional non-competitive enzyme-linked immunosorbent assay (ELISA) that a valence of the antibody obtained from the mouse ascites by purifying might reach $3.2 \times 10^5$, that was, when the antibody was diluted by $3.2 \times 10^5$ times, the solution measurement result was positive. It was measured by using a conventional indirect competitive ELISA that its sensitivity to 4,15-diacetoxyscirpenol was 3.08 ng/mL. Cross reactivity with other mycotoxins, T-2 toxin, HT-2 toxin, vomitoxin, 3-acetyldeoxynivalenol, ochratoxin, and fumonisin each were less than 0.01% (Table 1; FIG. 3). Specificity of the antibody might be evaluated by using cross reactivity. The monoclonal antibody from the DAS5G11E7 was measured by using the indirect competitive ELISA. Standard solutions in series concentrations were prepared from DAS, T-2 toxin, HT-2 toxin, DON, 3-ACDON, OTA, and $FB_1$, and added together with an equal volume of antibody into ELISA plates respectively to be incubated for 1 h. Other steps were the same as the indirect competitive ELISA. Concentrations of the foregoing toxin standards served as abscissas, and OD values B/B0 under 450 nm measured by a microplate reader served as ordinates, to draw a competitive inhibition curve. Cross reactivity was determined by calculating ratios of an IC50 value of DAS to an IC50 value of other toxins. The calculation formula was as follows:

$$CR\% = (IC50_{DAS}/IC50_{other\ toxins}) \times 100.$$

TABLE 1

| Cross reaction of DAS5G11E7 with other toxins | | | |
| --- | --- | --- | --- |
| Name of toxin | Structure | IC50 | Cross reactivity |
| DAS | (structure) | 3.08 | 100% |
| T-2 toxin | (structure) | >100,000 | <0.01% |

TABLE 1-continued

Cross reaction of DAS5G11E7 with other toxins

| Name of toxin | Structure | IC50 | Cross reactivity |
|---|---|---|---|
| HT-2 toxin | | >100,000 | <0.01% |
| DON | | >100,000 | <0.01% |
| 3-acetyl-DON | | >100,000 | <0.01% |
| $FB_1$ | | >100,000 | <0.01% |
| OTA | | >100,000 | <0.01% |

Figure 1:
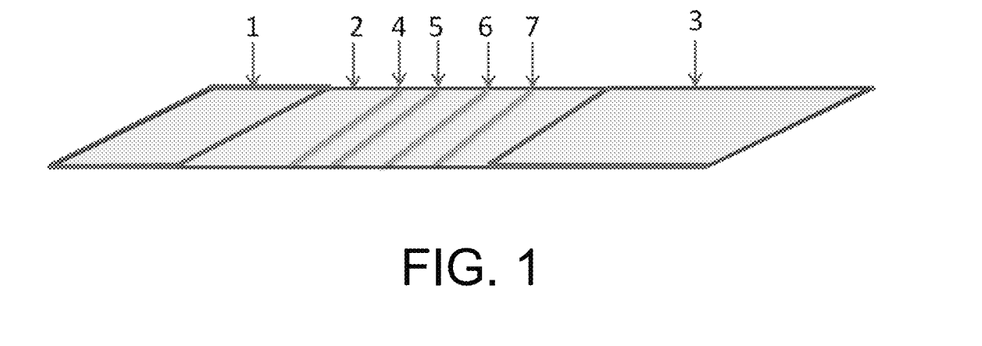
Figure 2:
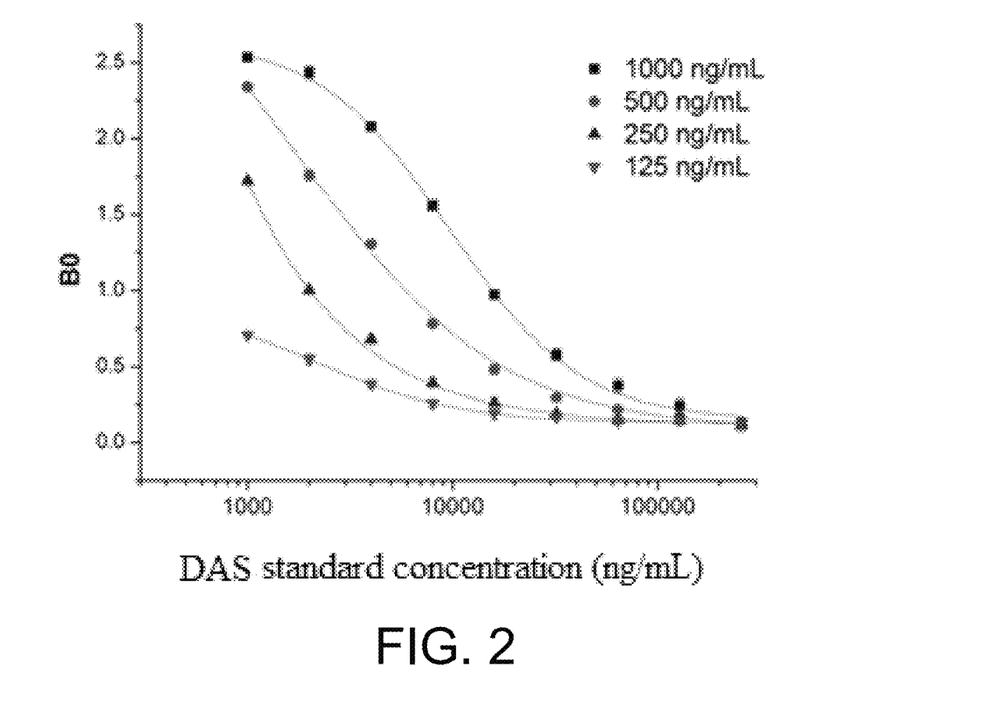

Affinity of the DAS5G11E7 was measured by using the indirect non-competitive ELISA. The ELISA plates were coated with DAS-OVA according to concentrations of 1.0 μg/mL, 0.5 μg/mL, 0.25 μg/mL, and 0.125 μg/mL, with 100 μL per pore, at 37° C. for 2 h. After blocking was performed for 1 h by using a blocking solution, the antibody diluted by PBS (a dilution factor of 1:2) was added into the ELISA plates. Other steps were the same as the indirect non-competitive ELISA. Measured OD450 values served as ordinates, and log values of antibody concentrations (mol/L) served as abscissas, to draw four S-shaped curves of four concentrations. A maximum OD value on the topmost of each S-shaped curve was found out, namely ODmax, and an antibody concentration corresponding to a 50% ODmax value of each curve was found out. Affinity constants of the antibody were calculated according to the formula Ka=(n−1)/2(n[Ab']t−[Ab]t) by grouping any two of the four concentrations into a group, where [Ab']t and [Ab]t were antibody concentrations corresponding to two 50% maximum OD values in each group, n was a multiple (including three ratios 1:2, 1:4, and 1:8) of a coated antigen concentration in each group, and six Ka values were obtained in total. The six obtained Ka values were averaged to obtain the affinity of an anti-4,15-diacetoxyscirpenol mouse ascites antibody by using the enzyme-linked immunosorbent assay (ELISA), which might reach $5.4\times10^8$ L/moL (FIG. 2).

Screening of hybridoma cell strain DAS5G11E7

1. Animal Immunization

BALB/c mice that were six to seven weeks old were immunized by a 4,15-diacetoxyscirpenol complete antigen DAS-BSA prepared in a laboratory. For the first immunization, the 4,15-diacetoxyscirpenol complete antigen and an equal volume of Freund's complete adjuvant were emulsified and subcutaneously injected at multiple points in necks and backs of the mice. The second immunization was performed four weeks later. A Freund's incomplete adjuvant and an equal volume of 4,15-diacetoxyscirpenol complete antigen were emulsified and injected in abdomens of the mice. The interval between the third immunization and the second immunization was 4 weeks, and the immunization manners were the same. The fourth immunization was performed 3 weeks after the third immunization, and the immunization manner was the same as that in the second immunization, that was, intraperitoneal injection. In the four immunizations, dosages were the same, that was, 70 μg for each mouse. For the first three immunizations, eight days to ten days after each immunization, blood was sampled from caudal vein, serum was separated out, and valences of the serums of the mice were measured by using the indirect ELISA. Eight days after the third immunization, tails were cut for blood sampling, and the mice corresponding to the serums with both relatively high valences and sensitivities were selected for the last enhanced immunization, with an immunization dosage twice the foregoing dosage.

2. Cell Fusion

Three days after the enhanced immunization, PEG with a weight percentage of 50% and a polyethylene glycol molecular weight of 1450 was used as a fusogen, and cell fusion was performed by using a conventional method, specifically including the steps: sacrificing the mice by cervical dislocation under aseptic conditions, taking out spleens, using a homogenizer to crush the spleens, separating out splenocytes by using a filter screen, mixing the splenocytes and murine myeloma cells SP2/0 according to a ratio of 5:1, centrifuging, resuspending mixed cells by using an RPMI-1640 basal medium, centrifuging, and discarding supernate; and adding 1 mL to 2 mL of 50% PEG within 1 min in total, adding 10 mL to 20 mL of RPMI-1640 basal medium along the wall, centrifuging, discarding supernate, resuspending fused cells at a tube bottom by using 20 mL of a cell complete medium containing 1% of HAT, adding suspended cells to 80 mL of a semi-solid medium, evenly mixing, adding the obtained mixture into a 6-pore cell culture plate, with 1.5 mL per pore, and culturing in a 37° C. carbon dioxide incubator. The cell complete medium containing 1% of HAT included: 20% (volume percentage) of fetal bovine serum, 75% (volume percentage) of RPMI-1640 basal medium, 1% (weight percentage) of L-glutamine, 1% (volume percentage) of HEPES, 1% (volume percentage) of double antibodies (10000 units per milliliter of penicillin and 10000 micrograms per milliliter of streptomycin), 2% (volume percentage) of growth factor (HFCS), and 1% (weight percentage) of hypoxanthine-aminopterin-thymidine (HAT) and methylcellulose, which was purchased from the sigma-Aldrich company.

Screening and Cloning of Cell Strain

When cell colonies grew to be visible to the naked eye two to three weeks after the cell fusion, clones were picked from the culture medium by using a micropipettor and transferred to a 96-pore cell culture plate to be cultured in HAT liquid. When cells grew to ⅔ height from the pore bottom, a culture supernate was sucked for detection. A two-step screening method was applied. In the first step, the indirect ELISA was used to screen out positive pores that were resistant to 4,15-diacetoxyscirpenol other than a carrier protein BSA. In the second step, indirect competitive ELISA was used to detect the positive pores screened out in the first step, and 4,15-diacetoxyscirpenol was used as a competitor to select the pores with both relatively large light absorption value and relatively high sensitivity (relatively large light absorption value meant that a final measurement value of a pore with the competitor of 0, that was, a positive control hole, was relatively large, and relatively high sensitivity meant that a competitor concentration at an inhibition ratio of 50%, that is, the $IC_{50}$ value was relatively small). Subcloning was performed by using a limiting dilution method. After the subcloning, the same two-step method was used to perform detection. After subcloning was repeatedly performed for 4-5 times, the hybridoma cell strain DAS5G11E7 was obtained. This hybridoma cell strain has already been preserved on Apr. 3, 2018 in China Center For Type Culture Collection (CCTCC), the preservation address is Wuhan University, Wuhan, China, and the preservation number is CCTCC NO: C201881.

Measurement of sequences of variable regions of anti-4,15-diacetoxyscirpenol monoclonal antibody, hybridoma cell strain DAS5G11E7 antibody (1) Extraction of total RNA: a total RNA extraction kit from the Tiangen company was used to extract, following the instructions, total RNA capable of producing the hybridoma cell strain DAS5G11E7;

(2) Synthesis of cDNA: with the total RNA obtained in the step (1) as a template and oligo(dT)15 as primers, reverse transcription was performed, following the SuperScript™-2II reverse transcriptase instructions, to synthesize a first strand of cDNA; where the primers oligo(dT)15 were purchased from Invitrogen; and (3) Cloning of variable region genes by a PCR method: based on conserved sites of mouse antibody gene sequences in GENBANK, primers were designed, and the cDNA was used as a template to amplify the antibody heavy chain and light chain variable region genes. The PCR procedure included: at 94° C. for 30 s, at 58° C. for 45 s, at 72° C. for 1 min, amplification for 30 cycles, and finally elongation at 72° C. for 10 min. After electrophoretic separation was performed on the PCR product by using 1% (weight percentage) of agarose gel, DNA segments were purified and recovered by using a kit and connected into a vector pMD18-T, *Escherichia coli* DH5a competent cells were transformed, positive clones were picked and sent to Shanghai Sunny Biotechnology Co., Ltd. for sequencing. For sequences of the primers, the sequences of the heavy chain variable region primers were 5'-CAG GTS MAR CTG MAG GAG TCW G-3'(22mer) and 5'-CAG GGG CCA GTG GAT AGA CAG ATG GGG G-3'(28mer), where S, M, R, and W were degenerate bases, M=A/C, R=A/G, S=G/C, and W=A/T; and the sequences of the light chain variable region primers were 5'-GAC ATC AAG ATG ACC CAG TCT CCA-3'(24mer) and 5'-CCG TTT TAT TTC CAG CTT GGT CCC-3'(24mer).

Resulting gene sequence results: the sequence of a heavy chain variable region coding gene was 351 bp in length and was shown as SEQ ID NO:1, and it was deduced that a heavy chain variable region encoded by the gene sequence was composed of 117 amino acids and was shown as SEQ ID NO:3 based on the obtained gene sequence. The sequence of a light chain variable region coding gene was 324 bp in length and was shown as SEQ ID NO:2, and it was deduced that a light chain variable region encoded by the gene sequence was composed of 108 amino acids and was shown as SEQ ID NO:4 based on the obtained gene sequence.

The anti-deoxynivalenol monoclonal antibody was preferably the anti-deoxynivalenol monoclonal antibody with an IC50 less than or equal to 15 ppb, for example, the anti-deoxynivalenol monoclonal antibody produced by Shandong Lvdu Bio-Sciences&Technology Co., Ltd. In this embodiment, the anti-deoxynivalenol monoclonal antibody from Shandong Lvdu Bio-Sciences&Technology Co., Ltd. was specifically used, and a sensitivity IC50 was 12 ppb.

The anti-T-2 toxin monoclonal antibody was preferably the anti-T-2 toxin monoclonal antibody with an IC50 less than or equal to 2 ppb (2 ng/mL), for example, the anti-T-2 toxin monoclonal antibody produced by Shandong Lvdu Bio-Sciences&Technology Co., Ltd. In this embodiment, the anti-T-2 toxin monoclonal antibody from Shandong Lvdu Bio-Sciences&Technology Co., Ltd. was specifically used, and a sensitivity IC50 was 0.8 ng/mL through detection.

Embodiment 4 Time-resolved fluorescence kit for synchronously detecting 4,15-diacetoxyscirpenol, deoxynivalenol, and T-2 toxin A time-resolved fluorescence kit for quantitatively detecting 4,15-diacetoxyscirpenol, deoxynivalenol, and T-2 toxin includes a fluorescence test strip, a reaction bottle containing an europium-labeled anti-4,15-diacetoxyscirpenol monoclonal antibody, an europium-labeled anti-deoxynivalenol monoclonal antibody, and an europium-labeled anti-T-2 toxin monoclonal antibody, and a sample diluent. The fluorescence test strip includes a paperboard, where a water absorption pad, a detection pad, and a sample pad are sequentially attached to one side of the paperboard from top to bottom; adjacent pads are connected in an overlapping manner at a joint, and an overlapping length is 1 mm; in the immunochromatography time-resolved fluorescence test strip, the water absorption pad is 38 mm in length and 4 mm in width, the detection pad is 25 mm in length and 4 mm in width, the sample pad is 15 mm in length and 4 mm in width, and an overlapping length of adjacent pads is 1 mm; and the detection pad uses a nitrocellulose membrane as a base pad, a transverse quality control line, a detection line 1, a detection line 2, and a detection line 3 are arranged on the nitrocellulose membrane from top to bottom, and the quality control line is coated with a rabbit antimouse polyclonal antibody.

Obtaining of the fluorescence test strip:

(1) Preparation of the water absorption pad

Water absorption paper was cut into the water absorption pad with a specification of 18 mm in length and 4 mm in width;

(2) Preparation of the detection pad

Coating of detection lines:

A coating solution with a concentration of 1 mg/mL was prepared from a 4,15-diacetoxyscirpenol coating antigen by using a coating buffer solution. A nitrocellulose membrane was transversely coated with the coating solution in a streak manner in a position 12 mm away from an upper edge of the nitrocellulose membrane to obtain a detection line, where a coating quantity of the coating antigen required for each centimeter of the detection line was 0.6 μg. Then, drying was performed at 37° C. for 60 min.

A coating solution with a concentration of 0.25 mg/mL was prepared from a deoxynivalenol coating antigen by using a coating buffer solution. The nitrocellulose membrane was transversely coated with the coating solution in a streak manner in a position 8 mm away from the upper edge of the nitrocellulose membrane to obtain a detection line, where a coating quantity of the coating antigen required for each centimeter of the detection line was 0.4 μg. Then, drying was performed at 37° C. for 60 min.

A coating solution with a concentration of 0.25 mg/mL was prepared from a T-2 toxin coating antigen by using a coating buffer solution. The nitrocellulose membrane was transversely coated with the coating solution in a streak manner in a position 8 mm away from the upper edge of the nitrocellulose membrane to obtain a detection line, where a coating quantity of the coating antigen required for each centimeter of the detection line was 0.4 μg. Then, drying was performed at 37° C. for 60 min.

The coating buffer solution included in each 10 mL: 0.1 g of bovine serum albumin (BSA), 0.002 g of sodium azide, 0.08 g of sodium chloride, 0.029 g of sodium phosphate dibasic dodecahydrate, 0.002 g of potassium chloride, and 0.002 g of monopotassium phosphate.

Coating of the quality control line:

A coating solution with a concentration of 0.25 mg/mL was prepared from a rabbit antimouse polyclonal antibody by using a coating buffer solution. The nitrocellulose membrane was transversely coated with the coating solution in a position 4 mm away from the detection lines in a streak manner to obtain the quality control line, where a coating quantity of the rabbit antimouse polyclonal antibody required for each centimeter of the quality control line was 0.4 μg. Then, drying was performed at 37° C. for 2 h.

The coating buffer solution included in each 10 mL:

0.1 g of bovine serum albumin, 0.002 g of sodium azide, 0.08 g of sodium chloride, 0.029 g of sodium phosphate dibasic dodecahydrate, 0.002 g of potassium chloride, and 0.002 g of monopotassium phosphate.

The nitrocellulose membrane was 25 mm in length and 4 mm in width.

(3) Preparation of the sample pad:

A fiberglass membrane was cut to a specification of 15 mm in length and 4 mm in width, put into a blocking solution to be soaked, taken out, and dried at 37° C. for 6 h to obtain the sample pad. Then, the sample pad was preserved in a dryer at room temperature.

The blocking solution was prepared from 2.9 g of sodium phosphate dibasic dodecahydrate, 0.3 g of sodium dihydrogen phosphate dihydrate, 1.0 g of Tween®-20, 1.0 g of polyvinyl pyrrolidone (PVPK-30), 0.25 g of EDTA, 0.5 g of bovine serum albumin (BSA), 0.02 g of sodium azide, and water that was added until a constant volume of 100 mL.

(4) Assembling of the fluorescence test strip:

The water absorption pad, the detection pad, and the sample pad were sequentially attached to one side of a paperboard from top to bottom to obtain the fluorescence test strip, where adjacent pads were connected in an overlapping manner at a joint, and an overlapping length was 1 mm.

Obtaining of the europium-labeled anti-4,15-diacetoxyscirpenol monoclonal antibody:

200 μL of an europium labeling reagent (a particle size of 100 nm, and a solid content of 1%) was added into 800 μL of a 0.2 mol/L boric acid buffer solution with a pH of 8.18. Oscillating and even mixing were performed. Ultrasonic processing was performed for 3 s. 40 μL of a 15 mg/mL EDC solution was added. Oscillating and even mixing were performed for 15 min. Centrifuging was performed at 13000 r/min and 10° C. for 10 min to remove supernate. For redissolving, 1 mL of a boric acid buffer solution was added. Oscillating and even mixing were performed. Ultrasonic processing was performed for 3 s. 20 μg of a 4,15-diacetoxyscirpenol monoclonal antibody was added to be evenly mixed. Processing was performed on a shaking table overnight at 250 r/min and 25° C. Centrifuging was performed again to remove supernate. For redissolving, 1 mL of a boric acid buffer solution that contains 0.5% of BSA was added. Oscillating and even mixing were performed. Ultrasonic processing was performed for 10 min. Processing was performed on a shaking table at 25° C. for 2 h to obtain a target product, namely the europium-labeled anti-4,15-diacetoxyscirpenol monoclonal antibody. The europium labeling reagent might be purchased from Shanghai Youni Biotechnology Co., Ltd., but was not limited thereto.

Obtaining of the europium-labeled anti-deoxynivalenol monoclonal antibody:

200 μL of an europium labeling reagent (a particle size of 100 nm, and a solid content of 1%) was added into 800 μL of a 0.2 mol/L boric acid buffer solution with a pH of 8.18. Oscillating and even mixing were performed. Ultrasonic processing was performed for 3 s. 40 of a 15 mg/mL EDC solution was added. Oscillating and even mixing were performed for 15 min. Centrifuging was performed at 13000 r/min and 10° C. for 10 min to remove supernate. For redissolving, 1 mL of a boric acid buffer solution was added. Oscillating and even mixing were performed. Ultrasonic processing was performed for 3 s. 20 μg of a deoxynivalenol monoclonal antibody was added to be evenly mixed. Processing was performed on a shaking table overnight at 250 r/min and 25° C. Centrifuging was performed again to remove supernate. For redissolving, 1 mL of a boric acid buffer solution that contains 0.5% of BSA was added. Oscillating and even mixing were performed. Ultrasonic processing was performed for 10 min. Processing was performed on a shaking table at 25° C. for 2 h to obtain a target product, namely the europium-labeled anti-deoxynivalenol monoclonal antibody. The europium labeling reagent might be purchased from Shanghai Youni Biotechnology Co., Ltd., but was not limited thereto.

Obtaining of the europium-labeled anti-T-2 toxin monoclonal antibody:

200 μL of europium labeling reagent (a particle size of 100 nm, and a solid content of 1%) was added into 800 μL of a 0.2 mol/L boric acid buffer solution with a pH of 8.18. Oscillating and even mixing were performed. Ultrasonic processing was performed for 3 s. 40 μL of a 15 mg/mL EDC solution was added. Oscillating and even mixing were performed for 15 min. Centrifuging was performed at 13000 r/min and 10° C. for 10 min to remove supernate. For redissolving, 1 mL of a boric acid buffer solution was added. Oscillating and even mixing were performed. Ultrasonic processing was performed for 3 s. 20 μg of a T-2 toxin monoclonal antibody was added to be evenly mixed. Processing was performed on a shaking table overnight at 250 r/min and 25° C. Centrifuging was performed again to remove supernate. For redissolving, 1 mL of a boric acid buffer solution that contains 0.5% of BSA was added. Oscillating and even mixing were performed. Ultrasonic processing was performed for 10 min. Processing was performed on a shaking table at 25° C. for 2 h to obtain a target product, namely the europium-labeled anti-T-2 toxin monoclonal antibody. The europium labeling reagent might be purchased from Shanghai Youni Biotechnology Co., Ltd., but was not limited thereto.

Application of the immunochromatography time-resolved fluorescence test strip to quantitatively detecting 4,15-diacetoxyscirpenol, deoxynivalenol, and T-2 toxin:

1. Construction of a curve of relationships between the ratio (T/C) of time-resolved fluorescence intensity of the detection lines to time-resolved fluorescence intensity of the quality control line on the fluorescence test strip and concentrations of 4,15-diacetoxyscirpenol, deoxynivalenol, and T-2 toxin:

(1) Sample preprocessing was performed on grains that were determined to be negative on 4,15-diacetoxyscirpenol, deoxynivalenol, and T-2 toxin by using high performance liquid chromatography (HPLC). To 25 g of a grain sample, 100 mL of a 80% methanol aqueous solution was added. Homogenizing and extracting were performed for 5 min. The extract was allowed to stand. The extract after standing was allowed to pass through double-layer filter paper. Filtrate was collected and diluted according to a ratio of 1:4.

(2) Labeling of standard substances was performed on the grain sample diluent to prepare a mixed standard solution. 4,15-diacetoxyscirpenol, deoxynivalenol, and T-2 toxin were added according to a ratio of 1:1:1 to prepare the mixed standard solution. Concentrations of standards were sequentially 1.5 ng/mL, 0.5 ng/mL, 0.15 ng/mL, 0.05 ng/mL, 0.015 ng/mL, and 0.005 ng/mL. Concentrations of 4,15-diacetoxyscirpenol standard solutions were 15 ng/mL, 5 ng/mL, 1.5 ng/mL, 0.5 ng/mL, 0.15 ng/mL, and 0.05 ng/mL respectively.

(3) Into a sample bottle, 200 μL of 4,15-diacetoxyscirpenol, deoxynivalenol, and T-2 toxin mixed standard solution was taken to be added. The solution was added into a sample reaction bottle containing europium-labeled monoclonal antibodies to be evenly mixed. One end of the sample pad of the fluorescence test strip was inserted into the reaction bottle for a reaction at 37° C. for 10 min. The product was loaded onto a machine to be detected. The detecting instrument was a time-resolved fluorescence immunoassay system and had an excitation wavelength of 365 nm and an emission wavelength of 615 nm. Ratios (T/C) of time-resolved fluorescence intensity of detection lines to time-resolved fluorescence intensity of quality control lines on the fluorescence test strips were detected.

(4) Concentrations of 4,15-diacetoxyscirpenol, deoxynivalenol, and T-2 toxin standards served as abscissas, and ratios (T/C) of time-resolved fluorescence intensity of detection lines to time-resolved fluorescence intensity of quality control lines corresponding to standard solutions with various concentrations served as ordinates, to obtain the curve of relationships through fitting. Effective detection ranges of the method included: a range of 0.5 ng/mL to 20 ng/mL for 4,15-diacetoxyscirpenol, a range of 1.0 ng/mL to 25 ng/mL for deoxynivalenol, and a range of 0.1 ng/mL to 10.5 ng/mL for T-2 toxin.

2. Spike and recovery test for quantities of 4,15-diacetoxyscirpenol, deoxynivalenol, and T-2 toxin contained in wheat samples:

To 20 g of wheat samples, 100 mL of a 80% methanol aqueous solution was added. Homogenizing and extracting were performed for 5 min. The extract was allowed to stand. The extract after standing was allowed to pass through double-layer filter paper. Filtrate was collected and diluted according to a ratio of 1:1.4,15-diacetoxyscirpenol (deoxynivalenol, and T-2 toxin) standards with concentrations of 1 ng/mL, 5 ng/mL, and 10 ng/mL were accurately added thereto respectively. Into a sample reaction bottle containing europium-labeled monoclonal antibodies, 200 μL of a to-be-tested sample detection solution was added to be evenly mixed. One end of the sample pad of the fluorescence test strip was inserted into the reaction bottle for a reaction at 37° C. for 10 min. The product was loaded onto a machine to be detected. The detecting instrument was a time-resolved fluorescence immunoassay system and had an excitation wavelength of 365 nm and an emission wavelength of 615 nm. Ratios (T/C) of time-resolved fluorescence intensity of detection lines to time-resolved fluorescence intensity of quality control lines on the fluorescence test strips were detected. Then, the ratios were substituted into a curve of relationships between the obtained ratios of time-resolved fluorescence intensity of detection lines to time-resolved fluorescence intensity of quality control lines on the fluorescence test strips and concentrations of standard substances, to obtain concentrations of substances including 4,15-diacetoxyscirpenol, deoxynivalenol, and T-2 toxin in the sample solution. Then, quantities of substances including 4,15-diacetoxyscirpenol, deoxynivalenol, and T-2 toxin contained in the sample might be obtained based on dilution ratios. It was measured that, in the wheat samples, spike and recovery rates of 4,15-diacetoxyscirpenol sequentially were 101.0%, 94.5%, and 90.1%; spike and recovery rates of deoxynivalenol sequentially were 98.9%, 95.5%, and 89.2%; and spike and recovery rates of T-2 toxin sequentially were 108.4%, 97.5%, and 93.0%.

What is claimed is:

1. A time-resolved fluorescence kit for synchronously detecting 4,15-diacetoxyscirpenol, deoxynivalenol, and T-2 toxin, comprising an immunoch evenly mixing an europium labeling reagent and a deoxynivalenol monoclonal antibody according to a mass ratio of 1:0.04-0.3, oscillating on a shaking table for 2 h to 4 h, centrifuging to remove supernate, and blocking redundant binding sites on a surface of the europium labeling reagent to obtain a target product, namely the europium-labeled anti-deoxynivalenol monoclonal antibody; and the europium-labeled anti-T-2 toxin monoclonal antibody is prepared by using the following method: evenly mixing an europium labeling reagent and a T-2 toxin monoclonal antibody according to a mass ratio of 1:0.04-0.3, oscillating on a shaking table for 2 h to 4 h, centrifuging to remove supernate, and blocking redundant binding sites on a surface of the europium labeling reagent to obtain a target product, namely the europium-labeled anti-T-2 toxin monoclonal antibody.

3. The time-resolved fluorescence kit according to claim 2, wherein the europium labeling reagent is activated before use, and the activation comprises: dissolving the europium labeling reagent in a boric acid buffer solution, oscillating and evenly mixing, adding an EDC solution, oscillating and activating for 15 min to 30 min, centrifuging at 10000 rpm to 15000 rpm, adding a boric acid buffer solution, oscillating and evenly mixing, and ultrasonically processing; wherein a blocking solution for blocking is a boric acid buffer solution that contains 0.5% to 1% of BSA.

4. The time-resolved fluorescence kit according to claim 1, wherein in the immunochromatography time-resolved fluorescence test strip, the water absorption pad is 15 mm to 35 mm in length and 3 mm to 5 mm in width, the sample pad is 12 mm to 18 mm in length and 2 mm to 5 mm in width, and an overlapping length of adjacent pads is 1 mm to 3 mm; on the detection pad in the immunochromatography time-resolved fluorescence test strip, a distance between the detection line close to the transverse quality control line and an upper edge of the nitrocellulose membrane is 15 mm to 20 mm, a distance between every two adjacent detection lines is 1.5 mm to 4.5 mm, and a distance between the detection line close to the transverse quality control line and the transverse quality control line is 4 mm to 10 mm; and the sample reaction bottle is a 1-5 mL bayonet bottle.

5. The time-resolved fluorescence kit according to claim 1, wherein on the detection pad in the immunochromatography time-resolved fluorescence test strip, a coating quantity of the 4,15-diacetoxyscirpenol-bovine serum albumin conjugate required for each centimeter of detection line is 0.4 μg to 0.8 μg, a coating quantity of the deoxynivalenol-bovine serum albumin conjugate required for each centimeter of detection line is 0.8 μg to 1.0 μg, and a coating quantity of the T-2 toxin-ovalbumin conjugate required for each centimeter of detection line is 0.8 μg to 1.0 μg; and a quantity of the freeze-dried product of the europium-labeled anti-4,15-diacetoxyscirpenol monoclonal antibody contained in the sample reaction bottle is 0.1 μg to 0.3 μg, a quantity of the freeze-dried product of the europium-labeled anti-deoxynivalenol monoclonal antibody contained in the sample reaction bottle is 0.2 μg to 0.4 μg, and a quantity of the freeze-dried product of the europium-labeled anti-T-2 toxin monoclonal antibody contained in the sample reaction bottle is 0.2 μg to 0.4 μg.

6. The time-resolved fluorescence kit according to claim 1, wherein an IC50 of the anti-deoxynivalenol monoclonal antibody is less than or equal to 15 ppb; and an IC50 of the anti-T-2 toxin monoclonal antibody is less than or equal to 2 ppb.

7. The time-resolved fluorescence kit according to claim 1, further comprising a sample diluent, wherein the sample diluent comprises 0.01% to 0.30% by volume of polysorbate 20, 0.5% to 1.5% by volume of sucrose, and 0.1% to 1% by volume of a bovine serum albumin aqueous solution.

8. The time-resolved fluorescence kit according to claim 1, wherein a preparation method for the time-resolved fluorescence test strip comprises the following steps:

(1) cutting water absorption paper into the water absorption pad;

(2) preparation of the detection pad:

preparing coating solutions with a concentration of 0.25 mg/mL to 2 mg/mL from the 4,15-diacetoxyscirpenol-bovine serum albumin conjugate, the deoxynivalenol-bovine serum albumin conjugate and the T-2 toxin-ovalbumin conjugate, coating the nitrocellulose membrane with the coating solutions at intervals in a streak manner to obtain the three detection lines, respectively, and drying at 37° C. to 40° C. for 30 min to 60 min; wherein a coating quantity of the 4,15-diacetoxyscirpenol-bovine serum albumin conjugate required for each centimeter of the detection line coated with the 4,15-diacetoxyscirpenol-bovine serum albumin conjugate is 0.2 μg to 0.8 μg, a coating quantity of the deoxynivalenol bovine serum albumin conjugate required for each centimeter of the detection line coated with the deoxynivalenol-bovine serum albumin conjugate is 0.2 μg to 1.0 μg, and a coating quantity of the T-2 toxin-ovalbumin conjugate required for each centimeter of the detection line coated with the T-2 toxin-ovalbumin conjugate is 0.2 μg to 1.0 μg;

on the detection pad in the immunochromatography time-resolved fluorescence test strip, a distance between the detection line close to the transverse quality control line and an upper edge of the nitrocellulose membrane is 15 mm to 20 mm, a distance between every two adjacent detection lines is 1.5 mm to 4.5 mm, and a distance between the detection line close to the transverse quality control line and the transverse quality control line is 4 mm to 10 mm; and preparing a coating solution with a concentration of 0.1 mg/mL to 0.45 mg/mL from the rabbit antimouse polyclonal antibody, and transversely coating the nitrocellulose membrane with the coating solution in a position 4 mm to 10 mm away from the detection lines in a streak manner to obtain the transverse quality control line, wherein a coating quantity of the rabbit antimouse polyclonal antibody required for each centimeter of the transverse quality control line is 0.4 μg to 0.8 μg; and then, drying at 37° C. to 40° C. for 30 min to 60 min;

(3) preparation of the sample pad:

putting a fiberglass membrane into a blocking solution to be soaked, taking out, and drying at 37° C. to 40° C. for 4 h to 10 h to obtain the sample pad, and then preserving in a dryer at room temperature; and (4) assembling of the immunochromatography time-resolved fluorescence test strip:

sequentially attaching the water absorption pad, the detection pad and the sample pad to one side of a paperboard from top to bottom to obtain the immunochromatography time-resolved fluorescence test strip, wherein adjacent pads are connected in an overlapping manner at a joint, and an overlapping length is 1 mm to 3 mm.

9. The time-resolved fluorescence kit according to claim 8, wherein during the preparation of the immunochromatography time-resolved fluorescence test strip, a coating buffer solution used to prepare the 4,15-diacetoxyscirpenol-bovine serum albumin conjugate coating solution, the deoxynivalenol-bovine serum albumin conjugate coating solution and the T-2 toxin-ovalbumin conjugate coating solution comprises in each 10 mL: 0.1 g of bovine serum albumin, 0.002 g of sodium azide, 0.08 g of sodium chloride, 0.029 g of sodium phosphate dibasic dodecahydrate, 0.002 g of potassium chloride and 0.002 g of monopotassium phosphate;
- a coating buffer solution used to prepare the rabbit anti-mouse polyclonal antibody coating solution comprises in each 10 mL: 0.002 g of sodium azide, 0.08 g of sodium chloride, 0.029 g of sodium phosphate dibasic dodecahydrate, 0.002 g of potassium chloride and 0.002 g of monopotassium phosphate; and
- the blocking solution used during the preparation of the immunochromatography time-resolved fluorescence test strip comprises in each 100 mL: 0.5 g to 2 g of ovalbumin, 2 g of sucrose, 0.02 g of sodium azide, 0.8 g of sodium chloride, 0.29 g of sodium phosphate dibasic dodecahydrate, 0.02 g of potassium chloride and 0.02 g of monopotassium phosphate.

10. Application of the time-resolved fluorescence kit according to claim 1 to detecting 4,15-diacetoxyscirpenol, deoxynivalenol and T-2 toxin, comprising: preprocessing a to-be-tested sample to obtain a to-be-tested sample solution, adding the to-be-tested sample solution into a sample reaction bottle, evenly mixing, inserting the time-resolved fluorescence test strip, carrying out a reaction at 37° C. for 6 min, and detecting by using a time-resolved fluorescence tester to obtain a ratio of time-resolved fluorescence intensity of the detection lines to time-resolved fluorescence intensity of the transverse quality control line on the immunochromatography time-resolved fluorescence test strip; based on a curve of respective relationships between the ratio of time-resolved fluorescence intensity of the detection lines to time-resolved fluorescence intensity of the transverse quality control line on the immunochromatography time-resolved fluorescence test strip obtained in advance and concentrations of 4,15-diacetoxyscirpenol, deoxynivalenol and T-2 toxin, obtaining quantities of 4,15-diacetoxyscirpenol, deoxynivalenol and T-2 toxin contained in the to-be-tested sample solution, and finally converting into quantities of 4,15-diacetoxyscirpenol, deoxynivalenol and T-2 toxin contained in the to-be-tested sample.

\* \* \* \* \*